United States Patent
Eckert et al.

(10) Patent No.: US 8,666,759 B2
(45) Date of Patent: *Mar. 4, 2014

(54) SYSTEM AND METHOD FOR EXCHANGING DOCUMENTS

(75) Inventors: John J. Eckert, West Hartford, CT (US); Paul Eckert, Cheltenham, PA (US)

(73) Assignee: Quixam, LLC, Cheltenham, PA (US)

( * ) Notice: Subject to any disclaimer, the term of this patent is extended or adjusted under 35 U.S.C. 154(b) by 1993 days.

This patent is subject to a terminal disclaimer.

(21) Appl. No.: 11/203,081

(22) Filed: Aug. 12, 2005

(65) Prior Publication Data

US 2007/0043592 A1 Feb. 22, 2007

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC ........................................................ 705/2–3
See application file for complete search history.

(56) References Cited

U.S. PATENT DOCUMENTS

| | | |
|---|---|---|
| 5,974,389 A | 10/1999 | Clark et al. |
| 2001/0041991 A1 | 11/2001 | Segal et al. |
| 2002/0007284 A1 | 1/2002 | Schurenberg et al. |
| 2002/0007287 A1 | 1/2002 | Straube et al. |
| 2002/0010679 A1 | 1/2002 | Felsher |
| 2002/0016721 A1 | 2/2002 | Mason et al. |
| 2002/0026332 A1 | 2/2002 | Snowden et al. |
| 2002/0035485 A1 | 3/2002 | Mita et al. |
| 2002/0052551 A1 | 5/2002 | Sinclair et al. |
| 2002/0062229 A1 | 5/2002 | Alban et al. |
| 2002/0111830 A1 | 8/2002 | Tahan |
| 2002/0120472 A1 | 8/2002 | Dvorak et al. |
| 2002/0156650 A1 | 10/2002 | Klein et al. |
| 2002/0169637 A1 | 11/2002 | Akers et al. |
| 2003/0014493 A1 | 1/2003 | Sakurai et al. |
| 2003/0050803 A1 | 3/2003 | Marchosky |
| 2003/0088441 A1 | 5/2003 | McNerney |
| 2003/0140044 A1* | 7/2003 | Mok et al. ........................ 707/10 |
| 2004/0034550 A1 | 2/2004 | Menschik et al. |
| 2004/0088192 A1 | 5/2004 | Schmidt et al. |
| 2006/0229918 A1* | 10/2006 | Fotsch et al. ...................... 705/3 |

* cited by examiner

*Primary Examiner* — Minnah Seoh

(74) *Attorney, Agent, or Firm* — Panitch Schwarze Belisario & Nadel LLP

(57) ABSTRACT

A method of exchanging documents among multiple businesses relating to common customers, including publishing documents relating to a first customer of a first business in a secure medium, determining whether the first customer is the same person as a second customer of a second business, and if the first customer is the same person as the second customer, granting access to the second business to the published documents.

21 Claims, 5 Drawing Sheets

SYSTEM AND METHOD FOR EXCHANGING DOCUMENTS

FIELD OF THE INVENTION

The present invention relates generally to document management. More particularly, it relates to sharing documents among multiple businesses.

SUMMARY OF THE INVENTION

A method of exchanging documents among multiple businesses relating to common customers, including publishing documents relating to a first customer of a first business in a secure medium, determining whether the first customer is the same person as a second customer of a second business, and if the first customer is the same person as the second customer, granting access to the second business to the published documents.

DETAILED DESCRIPTION OF THE PREFERRED EMBODIMENTS

Figure 1:
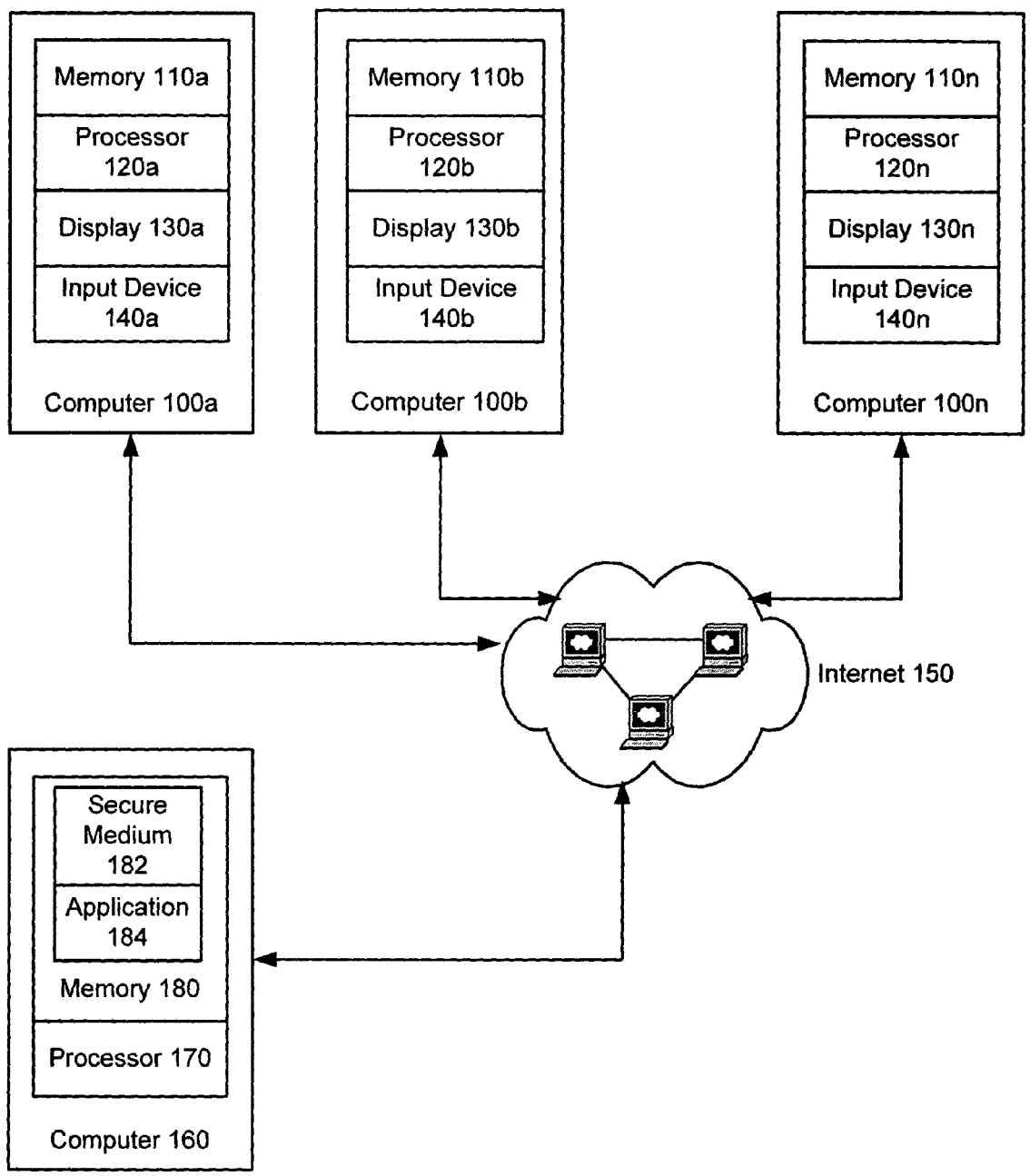
FIG. 1 is a block diagram of a system in accordance with a preferred embodiment of the present invention.

The following definitions are provided to aid in construing the claims of the present application:

BSC: A group of businesses, all of which businesses have at least one common customer. A first business can be BSC with respect to a second business relating to a first customer but not be BSC with respect to that business relating to a second customer.

Circle of Sharing: A group of businesses that are BSC with respect to a particular customer and that share certain documents relating to such customer, each business having affirmatively elected to join with respect to that customer. Each member of the Circle of Sharing is granted access to unrestricted documents published by other members relating to such common customer.

Document: For the purposes of the present application, an electronic file, such as, for example, a pdf or html file, containing text, images, sound, or video, among other formats, or any combination of such (or other) formats, whether or not additional matter is present in the file. The document can but need not be a scanned paper document or the electronic equivalent of a paper document.

Global: For purposes of the present application, global encompasses all published documents with granted permissions available to a business.

Grant Access/Send Reference: For purposes of the present application, granting access to data shall include granting access to data, such as by providing a database permission, password, or other means of accessing local or remote data or documents, sending a reference or a link to documents or data, sending original data or documents or copies thereof, or any other means of providing the contents of the applicable documents or data to the relevant individual or other entity. Sending a reference shall have the same meaning as granting access for purposes of the present application.

HIPAA: The Health Insurance Affordability and Accountability Act of 1996, as amended.

Hospital: For the purposes of the present application, any hospital or subdivision thereof, including a hospital department, such as a radiology department.

Limited: A user or class of users have limited rights when such users have a subset of the otherwise available rights with respect to documents or other data. For example, a user can be limited to accessing data relating to one or more customers or practitioners only. Other users can be limited to being only able to load data, but not to view data, or to view data, but not to load data. In some embodiments hereunder, limited rights are applicable only at the local level, while in other embodiments, they are also applicable at the global level.

Local: For purposes of the present application, local encompasses only documents uploaded, stored on, or otherwise provided to a system by a business and not documents uploaded, stored on, or otherwise provided to the system by other businesses.

Permanent Record: Documents that are published and identified to relate to the business customer.

Practitioner: For purposes of the present application, any individual granted authority by a practice to author a document, including a health care professional, such as a physician, physician's assistant, or nurse practitioner.

Provider of Nursing Services: For the purposes of the present application, any entity providing nursing services that is not a hospital or a medical practice. For example, this term includes nursing homes and home health care agencies.

Publication: For purposes of the present application, a document is published when it is uploaded, stored, or otherwise provided to a secure medium, whether or not access to the document is ever granted to any other business or person and even if the document is marked as restricted.

Restricted: For purposes of the present application, a document is restricted if the business publishing it marks it as restricted at the time of publication or at a subsequent time and remains restricted until such time as such business marks it as no longer restricted (or "unrestricted").

Secure Medium: Any computerized storage system, including but not restricted to a database system, that includes safeguards to prevent unauthorized users from gaining access to such system, whether or not such safeguards are completely effective. Preferably, secure file transport methods are utilized for uploading and downloading data to the secure medium.

Tombstone: An indication of status as a prior member of a Circle of Sharing. Grayed out text, for example, can be used as a Tombstone.

Referring generally to FIGS. 1 through 5, in certain preferred embodiments of the present invention, documents can be exchanged through granting database permissions either on an explicit share or an implicit share basis. In an explicit share, a first user designates the sharing user or users. This designation can be accomplished by selecting such user or users from a list and simply granting the requisite database rights, by sending references to the documents by a secure form of e-mail, or by other means. In an implicit share, a second user obtains rights to one or more documents automatically. For example, the second user can obtain such rights as a result of the first user obtaining such rights or as a result of the first user providing such one or more documents to a database. A Circle of Sharing is a form of implicit share.

Referring specifically to FIG. 1, a system in accordance with a preferred embodiment of the present invention is illustrated. Computers 100a through 100n are located at or used by businesses participating in an embodiment of the present invention. Each of computers 100a through 100n includes at least memory 110, processor 120, display 130, and input device 140. Memory 110 can be permanent storage, such as a hard drive, temporary memory, such as random access memory (RAM), or a combination thereof. Processor 120 can be any Pentium processor, although other microprocessors can also be used, including microprocessors used MacIntosh and PocketPC computers, for example. Display 130 can be a standard cathrode ray tube (CRT) monitor or liquid crystal display (LCD), such as a standard seventeen inch color CRT monitor, although a wide array of displays can be used. Input device 140 can be a keyboard, keypad, writing tablet, mouse, trackball, touchpad, touchscreen, microphone for a voice control system, or other input device, although a combination of keyboard and mouse is widely available. A Dell Pentium 4 desktop system such as the Dell Dimension 3000 is an example of one of many computers that would be satisfactory under many embodiments for use as computer 100(*a-n*). In certain embodiments hereunder, computer 100(*a-n*) should be capable of running an Internet browser and plug-ins, such as Adobe Acrobat Reader.

Computer 160 is one or more computers including memory 180 and processor 170. Memory 180 includes permanent storage, such as (but not limited to) a hard drive. Processor 170 can be any Pentium processor, although other microprocessors can also be used. A Dell Pentium 4 desktop system such as the Dell Dimension 3000 is an example of one of many computers that would be satisfactory under many embodiments for use as computer 160. Computer 160 is a centralized server that can optionally be hosted at multiple sites.

Computers 100a through 100n and computer 160 are connected to Internet 150. Each computer can be connected in the same manner or some computers can be connected differently. Computers 100a through 100n and 160 can be connected by dialup modem, by broadband connection (such as cable modem, ISDN, T-1, or T-3), or indirectly through a network to a computer that is connected to the Internet.

Memory 180 includes a secure medium 182, which is used to store documents to be exchanged among multiple businesses as described below with respect to the method illustrated in FIG. 2. Secure medium 182 can be a relational database, such as Oracle Database 10g or Microsoft SQL Server 2000 Enterprise Edition, a distributed database, or even (particularly in the case of a group of businesses using comparatively few documents) a simple collection of files in a directory tree format, such as an operating system directory tree format (provided that there are adequate protections against unauthorized access). In some embodiments, data is stored using structured data types. Any other type of secure medium can also be used. A document is published to the secure medium by uploading it securely to the secure medium or otherwise storing it on or providing it to the secure medium. Memory 180 also includes application 184, which implements the method illustrated in FIG. 2. In some embodiments hereunder, a portion of application 184 is instead stored in memories 110. For example, the user interface relating to the method can be stored locally in memories 110a through 110n while the remainder of the application is stored in memory 180.

In alternative embodiments of the present invention, computers 100a through 100n can connect to computer 160 by means other than the Internet, such as through a network or by direct modem to modem communication. In yet other embodiments of the present invention, computer 160 is not present and computers 100a through 100n communicate directly with each other (by means of the Internet or otherwise). In yet other embodiments, only a single computer is used and all data is stored on it.

Figure 2:
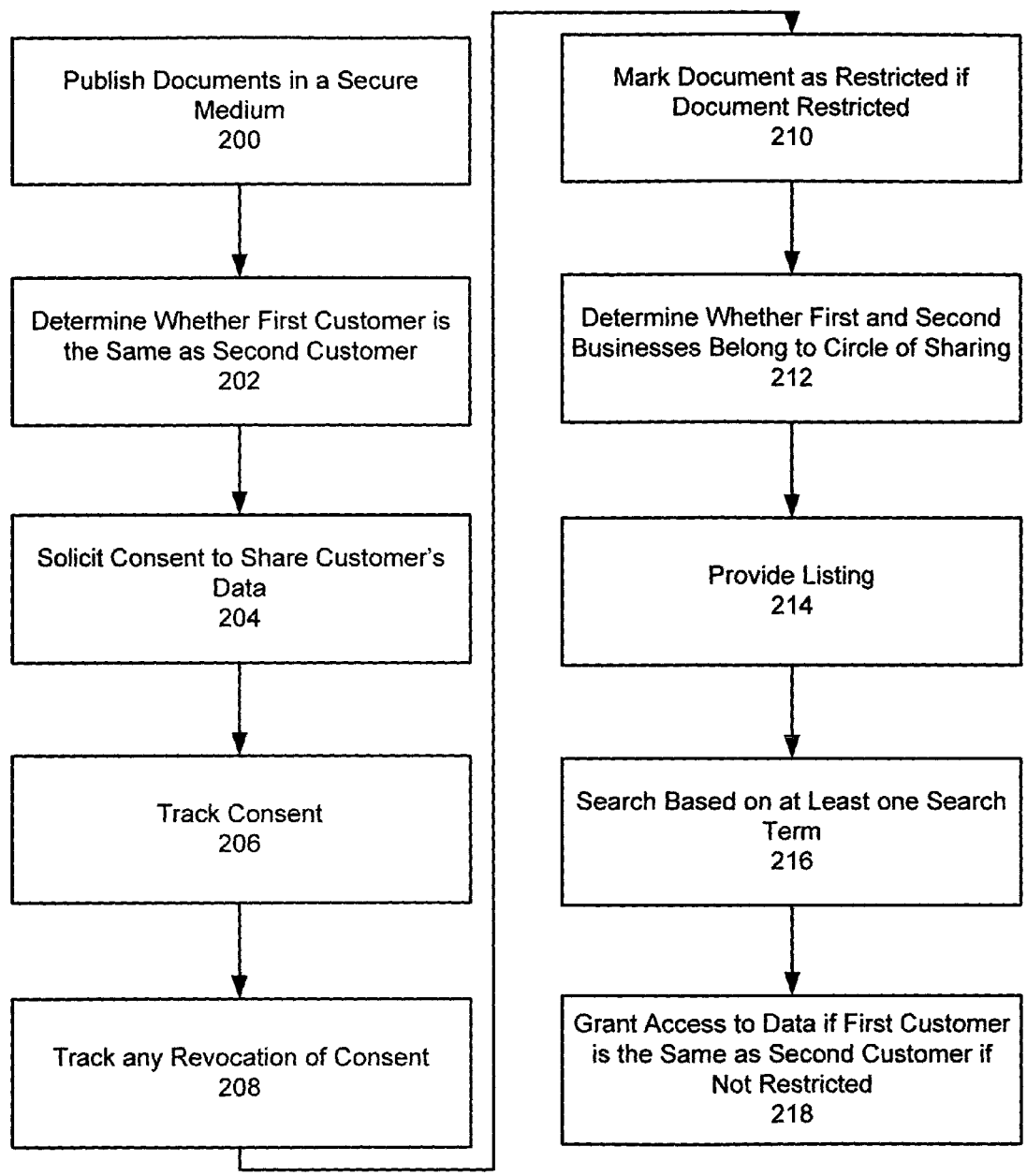
FIG. 2 is a flow chart illustrating a first method in accordance with a preferred embodiment of the present invention.

Referring to FIG. 2, a flow chart illustrating a method in accordance with a preferred embodiment of the present invention is set forth. In step 200, one or more documents relating to a first customer of a first business are published in a secure medium. The business, which can, but need not, be a medical practice, can publish one, some, or all of its documents relating to a particular customer. It can also, but need not, at the same time publish documents relating to other customers.

In step 202, it is determined whether the first customer of the first business is the same person as a second customer of a second business. The first and the second business can, but need not, be in the same field. For example, the first and second business can both be medical practices, or the first business can be a medical practice and the second business can be a pharmacy, laboratory, health insurance company, etc. The first and second customers can, but need not, be patients.

In some implementations of the present invention, published documents or references thereto are sent to other businesses when specifically directed to such businesses, such as, for example, by attaching such documents or references thereto to a secure form of electronic mail, as is described below. In other implementations of the present invention, published documents or references thereto are sent to other businesses by means of a Circle Of Sharing as is also detailed below. In the first case, it is only necessary to check whether the recipient business (or the business employing the recipient) has a customer who is the same person as the first customer. One method of determining whether the first and second customers are the same person is described below. In the second case, it is necessary to perform this check with respect to each member of the Circle Of Sharing. This can be accomplished, for example, by verifying whether each customer is a member of a Circle Of Sharing with respect to the first customer.

In step 204, the customer's consent to the sharing of his or her data is solicited. In the medical context, this comprises requesting that each patient of each medical practice consent to the sharing of such patient's medical records at that medical practice. This consent can be solicited by means of a written or digital form, especially a form requesting that the patient waive certain protections as authorized by HIPAA. In some embodiments of the present invention, consent is solicited repeatedly, evenly if previously granted. In certain embodiments of the present invention, step 204 is omitted.

In step 206, whether a customer has consented to the sharing of his or her data is tracked. Such consent can be tracked by entering into a database whether a customer has consented to share or refused each time the customer is solicited. In certain embodiments of the present invention, step 206 is omitted, especially in embodiments in which step 204 is omitted.

In step 208, if a revocation of any previously granted consent to the sharing of a customer's data is received, such revocation is tracked. Such revocation can also be tracked by means of a database entry. In certain embodiments of the present invention, step 208 is omitted, especially in embodiments in which step 204 is omitted.

In some embodiments of the present invention, if a customer does not consent to the sharing of his or her data, or revokes a previously granted consent, access is denied to (a)

all documents relating to such customer published after the refusal or revocation and (b) all documents relating to such customer published before the refusal or revocation but not shared with any other business. In other embodiments, such refusal or revocation has no effect. In other embodiments, such refusal or revocation applies only to documents marked as restricted. In yet other embodiments, the effect of such refusal or revocation is determined by each business. For example, in the medical context, HIPAA restricts the sharing of patient documents without patient consent; however, a practitioner retains the right to share patient documents without patient consent in limited circumstances in the course of patient treatment. Thus, in certain embodiments of the present invention, providing flexibility to each business can be useful.

In step 210, a document can be marked as restricted by a business. A specific document can be marked as restricted, all documents relating to a patient can be marked as restricted, or all documents of a certain type (such as HIPAA consent forms and administrative documents). In some embodiments of the present invention, marking a document as restricted prevents it from being shared at all outside the local business. In other embodiments, a restricted document is shared unless consent to share is refused or revoked. In other embodiments, step 210 is not performed or if performed has no effect.

In step 212, it is determined whether the first and second businesses are members of a Circle Of Sharing. Step 212 can be performed by verifying the underlying facts or by verifying status, for example, by performing a database lookup if the underlying facts have previously been determined. If a Circle Of Sharing exists with respect to the first customer and the first and second businesses are both members of it, then in step 218, not only are the currently published documents shared, but in many embodiments, other documents relating to the same customer as well. In some embodiments, all unrestricted documents previously, concurrently, or subsequently published by either the first or second businesses are shared between the first and second businesses; in addition, unrestricted documents previously, concurrently, or subsequently published by other businesses that are members of the Circle Of Sharing are provided to the first and second businesses as well. Moreover, unrestricted documents, whenever provided, authored by non-members of the Circle Of Sharing, but provided to one or more members of the Circle Of Sharing are also provided to the first and second businesses. Finally, any other documents, such as restricted documents that were nevertheless shared, whenever provided, authored by non-members of the Circle Of Sharing, but provided to one or more members of the Circle Of Sharing are also provided to the first and second businesses. In different embodiments of the present invention, different subsets of the above documents are shared or provided among members of a Circle Of Sharing. While maximal sharing of documents is appropriate in certain embodiments hereunder, in others a lesser degree of sharing is more desirable. In certain embodiments of the present invention, step 212 is omitted.

In step 214, a listing of one or more of all of the businesses, employees, or practitioners, or a subset of one or more thereof, listed in a database in the secure medium can be published on the secure medium. Examples of subsets include all practices or all physicians in a particular Circle Of Sharing. However, in some embodiments hereunder, in order to satisfy specific concerns, such as privacy concerns arising under HIPAA, certain listings can only be visible to defined individuals. For example, listings of practices or physicians participating in a particular Circle Of Sharing are only provided to members of the same Circle Of Sharing. In one preferred embodiment, listings of practices participating in a particular Circle Of Sharing include the names of practices formerly participating in that Circle Of Sharing (such as in the form of a tombstone), but such names of formerly participating practices are only provided to, or made visible to, practices participating in a Circle Of Sharing that at the time of the provision of the listings of practices include at least one practice participating in such Circle of Sharing at the time of participation of such former participants. In certain embodiments of the present invention, step 214 is omitted.

In step 216, a search can be performed of either global or just local documents based on at least one search term entered by a user, such as a practitioner. The search term or terms can include a term related to the customer's identity (such as the customer's name, social security number, etc.), a term relating to a class of documents (such as the name of a type or class of test), a term relating to a customer problem (such as a patient diagnosis), a term relating to a customer source (such as a referring physician), a term relating to the customer's status or condition (such as age or mental health), etc. Each document can further be labeled with metadata, such as, in the case of medical patient records, diagnostic codes, procedures codes, patient codes, etc. The search terms can then include such metadata, full text, and structured data. If the search is local, only local documents are searched and if the search is global, all permitted documents are searched. In certain embodiments, the user can elect to perform a limited search (such as a search encompassing local documents relating to a single practitioner only) as a third option. The results are then returned to the user. In some embodiments, full text searching of some or all documents is also enabled. In certain embodiments of the present invention, step 216 is omitted.

Whether the first customer and the second customer are the same person can be determined by many methods. For example, only the customers' names or the customers' social security numbers can be compared. A single comparison sharply increases the risk of error. For example, if only social security numbers are used, a transcription error can result in data relating to two different persons being combined. Similarly, many people have common names (such as "John Smith"), while slight errors in recording less common names can result in the same person being treated as two people. Using only name and social security number decreases the risk of inappropriately combining data but increases the risk of treating individual persons as multiple entities. Nevertheless, this latter method is a sufficient method for the purposes of the present invention in many contexts.

An improved method utilizes current and historical information as well, such as one or more of the customer's former names (if any), current and former address, secondary address, current and former telephone number, secondary telephone number, secondary e-mail address, and current and former e-mail address. One of the difficulties of utilizing information such as a customer's address for purposes of determining a customer's identity is that customers tend to move frequently, change telephone numbers frequently, etc. Nevertheless, if a customer's complete address history is matched against another person's complete address history and those address histories substantially match, the likelihood that the two persons are the same is extremely high if they also have the same social security number (or the same name and a social security number that is the same but for one digit or two transposed digits). In addition, or in the alternative, biorhythmic data, such as fingerprints, handprints, retinal scans, etc. can be used to aid in matching, and a historical log of such data can be kept to increase the likelihood that a useful sample will be available on file for matching.

In a preferred embodiment if the first customer and the second customer are initially determined to be the same customer, but are later determined to be different customers, any records or database entries indicating such false identity are corrected, any false matches or shares are broken, and any incorrectly shared documents are segregated. The first and second customer can be incorrectly determined to be the same customer due to a failure of an algorithm for matching customers, a transcription or other input error, etc. Incorrectly shared documents can be segregated, for example, by marking such documents as being of a different worktype.

In step 218, access is granted to the published document or documents if the first customer is the same person as the second customer. Access can be granted though granting a database permission or by sending a link to the published document or documents to the second business (or even by sending actual copies of the published documents to the second business). If it has been established that both the first and second businesses are members of an existing Circle Of Sharing in step 212, then not only is access to the current published document or documents granted to the second business, but also access to past and future published document or documents published by the first business with respect to the first customer, to the extent such document or documents were (or are) unrestricted by the authoring business. Indeed, access to past and future published document or documents published by any member of the Circle Of Sharing is granted to the second business and reciprocal rights are granted to the first business. If it has not been established that both the first and second businesses are members of an existing Circle Of Sharing in step 212 (but the first customer is a common customer of the first and second businesses), then access is granted to the published document or documents only.

In certain embodiments hereunder, until a document has been shared with another business through a grant of access as described in this step 218 or otherwise, that document can be marked as restricted or otherwise made unavailable for sharing through the grant of access. Once a grant of access has occurred, however, the grant is irrevocable and subsequent sharing cannot be prevented other than through voluntary means. In other embodiments, grants of access are revocable if shared documents have not been accessed even if already shared. In other embodiments, grants of access are not irrevocable. In yet other embodiments, once a document has been published it is irrevocably available for sharing.

If after a Circle Of Sharing is created and documents are published in the secure medium, the Circle Of Sharing ceases to exist for any reason (such as the withdrawal of the participating businesses due to their common customer's revocation of consent to share data), the published documents will cease to be shared to businesses that do not already have rights to them. If thereafter, one or more new businesses join a Circle Of Sharing with respect to such customer, such new business or businesses will remain unable to access the previously shared documents by means of the Circle Of Sharing. However, if one or more previously participating businesses rejoin a Circle Of Sharing with respect to such customer, the previously published documents (to the extent unrestricted) will be shared among any previously participating businesses and any other businesses also joining the Circle Of Sharing.

In certain embodiments hereunder, specific businesses, or specific users at specific businesses, or entire classes of users or businesses can be granted limited rights with respect to specific documents or classes of documents. In such embodiments, it is necessary to verify that each user has the requisite rights to perform the intended action on a document before granting permission to do so. For example, in one embodiment, hospital laboratories are granted only limited rights with respect to documents relating to their own customers: such laboratories are only permitted to load documents (such as laboratory results) to the secure medium, but not to view other documents relating to the same patients. In that embodiment, pharmacies, on the other hand, are permitted to view documents relating to their customers loaded by other businesses (e.g., portions of the customers' patient records containing lists of medications currently or previously prescribed for the patient, medical conditions affecting the customers, and possible drug allergies suffered by the customers) but are not permitted to load documents to the secure medium.

In certain embodiments hereunder, with respect to each action taken by a user with respect to the system, a log of such action is maintained to ensure that an audit trail exists. For example, in a medical records implementation of the present invention, it is desirable to be able to determine after the fact what records any particular user inspected or created and any document attributes that may have been altered, who viewed the records of a particular patient, what access rights a particular user was granted, and who granted a particular user access rights.

In certain embodiments hereunder, a business can grant access to its customers to view their data. A business can grant such access by, for example, (a) permitting a customer to view the results of a database query returning data relating only to that customer on a computer terminal (taking any security measures necessary to prevent the customer from viewing other customers' data, such as locking the terminal or applicable software program), (b) downloading a copy of the data relating to the customer to a floppy disk, CD-ROM, DVD, or other form of storage, or downloading a copy of the data to a computer belonging to the customer, or (c) providing the customer with a user ID sufficient to allow the customer to access that customer's data. The business can provide data either on a local basis (i.e. data relating only to such business) or on a global basis (i.e. all data relating to such customer to which the business has access, even if it relates to other businesses). In yet other embodiments, a customer can be granted a system-wide user ID to access data relating to such customer on a global or more restricted basis.

Figure 3:
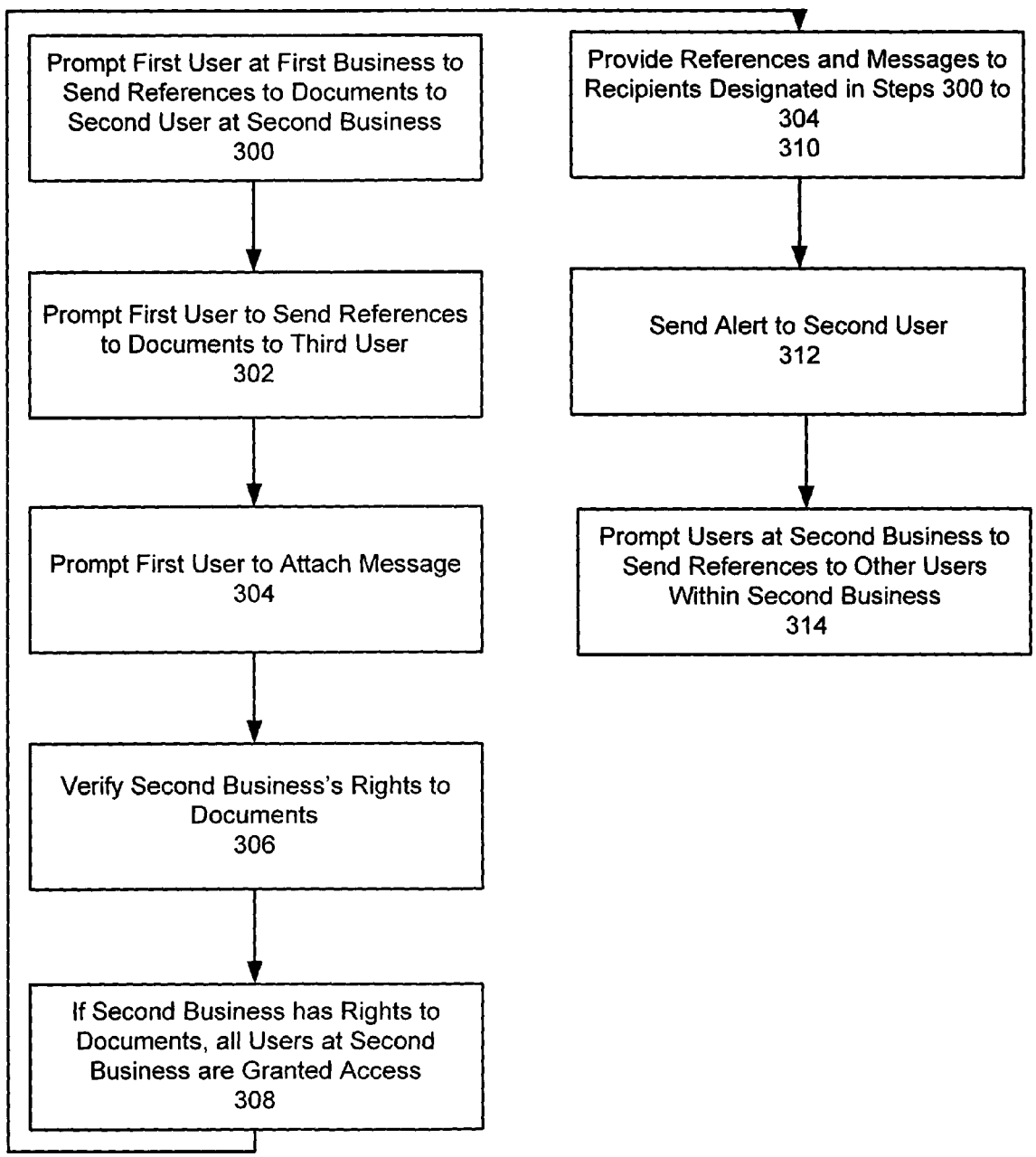
FIG. 3 is a flow chart illustrating a second method in accordance with a preferred embodiment of the present invention.

Referring to FIG. 3, a flow chart illustrating a second method in accordance with a preferred embodiment of the present invention is set forth. In step 300, a first user at a first business is prompted to send one or more references to one or more documents relating to a first customer of a first business to a second user at a second business. In some embodiments hereunder, the user is only granted the option to send a reference to a single document.

In step 302, the first user is prompted to send the one or more references to one or more documents relating to the first customer to a third user. The third user can be located at either the second business or a third business. Step 302 can be repeated as many times as desired. In some embodiments hereunder step 302 is omitted.

In step 304, the first user is prompted to attach a message to the one or more references being sent. The first user can optionally be prompted to attach a separate message to each user receiving the references in step 302. In some embodiments hereunder step 304 is omitted.

In step 306, the second business's rights to the document or documents are verified. In certain preferred embodiments hereunder, the second business has rights to documents if the documents relate to a customer of the second business. Whether the first customer is a customer of both the first and second businesses can be determined as described above in connection with the method illustrated in FIG. 2.

In step 308, if the second business has rights to the document or documents, all users at the second business are granted access to the document or documents. Similarly, if references to such document or documents have been sent to users at other businesses, this step is performed with respect to such businesses. In some embodiments hereunder, all users are not granted access to the document or documents even if the second business has rights to the document or documents unless a profile has been created in the second business's database relating to the customer to which such document or documents relate.

In step 310, the reference or references and any attached messages are provided to the users to whom they were sent in steps 300 through 304. Regardless of whether the businesses with which such users are associated have rights to the first customer, such users can view the messages and the documents to which the references relate. If the businesses have rights to the documents, then all users at such businesses can access such documents. The businesses have rights to the documents if the businesses have one or more common customers (in some embodiments one or more common customers set up in their respective databases) to which the documents relate, for example if they belong to one or more Circles of Sharing. If the businesses lack rights to the documents at the time but acquire them later, then all users at such businesses can access such documents when such businesses acquire such rights. Optionally, whether the recipient user or users have viewed the reference or references can be recorded. In some embodiments, this information is provided with respect to local users only; in other embodiments, this information is available globally.

In step 312, an alert is sent to the second user that the one or more references have been sent. This alert can be a facsimile, page, e-mail, automated telephone call, text message, short message service (sms), or other form of alert. In some embodiments hereunder step 312 is omitted.

In step 314, in certain embodiments hereunder, users at the second business are prompted to send the one or more references to other users at the second business if the second business has rights to the documents to which the one or more references relate. Optionally, such one or more references can be combined with one or more references to documents authored at such second business, or received from other sources.

In certain embodiments hereunder, the second user upon receiving the one or more references and any attached messages, is prompted to add automatically each customer to whom the one or more references relate as customers of the second business. Thus, for example, if a referring business sent references to documents relating to one or more customers being referred to a second business, the second business could be prompted to add such one or more customers into its computer system without the need for manual data entry, allowing full data sharing before the referred customer or customers first visit the second business.

In certain embodiments hereunder, each business can be prompted to establish a profile that identifies a recipient of references to documents and messages with respect to each customer of the business. Thereafter, other businesses can route references to documents and other messages to a general electronic address corresponding to such business, rather than a specific user at the business, and the references and other messages will be rerouted automatically. If the user then becomes temporarily or permanently unavailable, the references and other messages can be rerouted to another user, or rerouted among several users.

Figure 4:
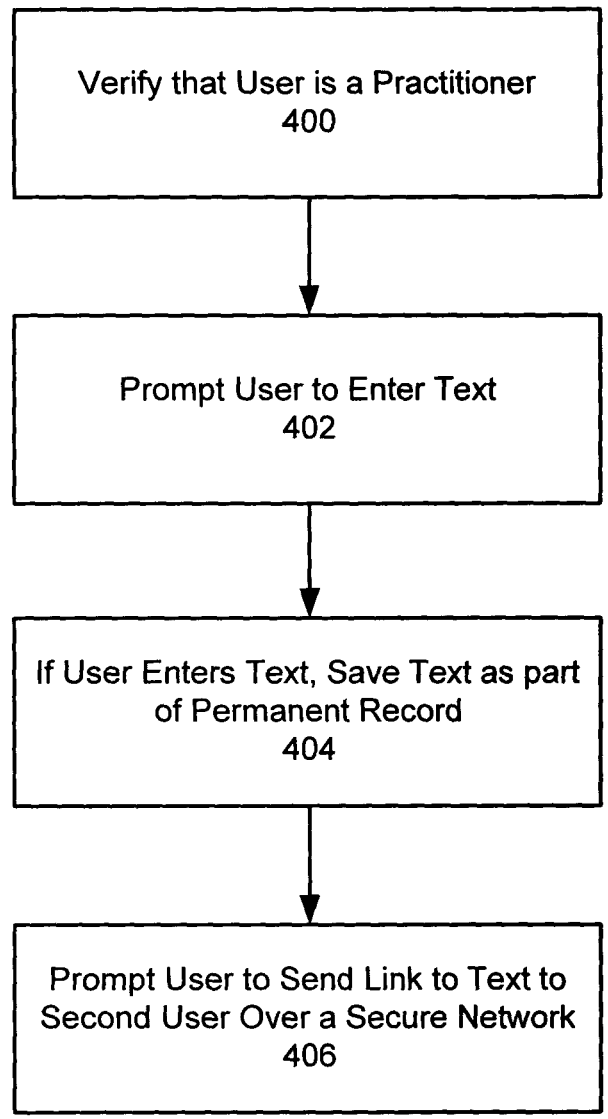
FIG. 4 is a flow chart illustrating a third method in accordance with a preferred embodiment of the present invention.

Referring to FIG. 4, a flow chart illustrating a third method in accordance with a preferred embodiment of the present invention is set forth. In step 400, it is verified that the user is a practitioner. This verification can be accomplished by comparing login and password (or biometric or other) information to verify that the user is on a previously stored list of practitioners. In step 402, the practitioner is prompted to enter text. Step 402 can be accomplished by presenting the practitioner with a standard text box in a user interface or customized user templates in a user interface. In step 404, the practitioner is prompted to submit the text as a portion of a permanent record. This permanent record can be a patient record. For example, the practitioner can be prompted to add the text to a patient's record as a note, prescription, laboratory requisition, etc. The practitioner can be provided with a list of patients or a search mechanism for selecting patients, such as by typing in names or other identifying information. In step 404, if the practitioner submits the text, the text is saved as a portion of the permanent record. In step 406, the practitioner is prompted to send a link to the text to a second practitioner, pharmacy, laboratory, etc. over a secure network.

Figure 5:
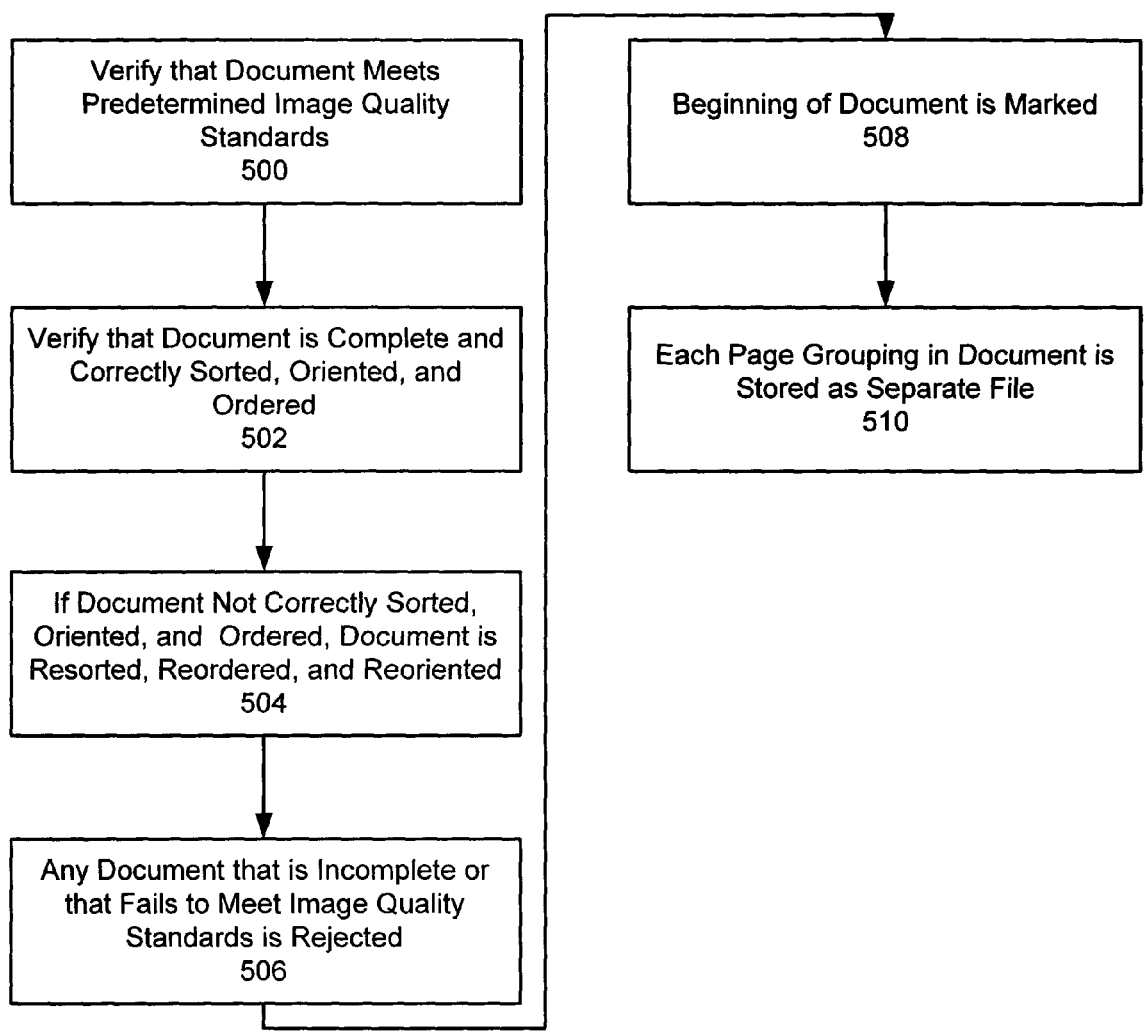
FIG. 5 is a flow chart illustrating a fourth method in accordance with a preferred embodiment of the present invention.

Referring to FIG. 5, a flow chart illustrating a fourth method in accordance with a preferred embodiment of the present invention is set forth. In step 500, it is verified that a document meets predetermined image quality standards. In step 502, it is verified that the document is complete and correctly sorted, ordered, and oriented. In step 504, if the document is not correctly sorted, ordered, and oriented, it is resorted, reordered, and reoriented. In step 506, any incomplete document or document failing to meet the predetermined image quality standards is rejected. In step 508, an indication is marked at the beginning of the document. In step 510, each page grouping from the first page of the document to but not including the first page of the following document is stored as a separate file with an identifier relating to the relevant customer.

Appendix A includes selected documentation relating to one possible implementation of certain aspects of the present invention and is incorporated herein by reference. Its inclusion is not intended in any way to restrict the scope of the present invention, but merely to provide additional guidance as to how some aspects of the present invention can be implemented.

The present invention may be embodied in other specific forms without departing from the spirit or essential attributes of the invention. Accordingly, reference should be made to the appended claims, rather than the foregoing specification, as indicating the scope of the invention.

APPENDIX A

Table of Contents

Introduction
1.1 Purpose
1.2 Document Conventions
1.3 Intended Audience and Reading Suggestions
1.4 Product Scope
1.5 References
2. Overall Description
2.1 Product Perspective
2.2 Product Functions
    2.2.1 System Administrative Functions
    2.2.2 Practice Administrative Functions
    2.2.3 Practice Management Functions
    2.2.4 Document Management Functions 2.3 User Classes and Characteristics
2.4 Operating Environment
2.5 Design and Implementation Constraints
2.6 Assumptions and Dependencies
    2.6.1 PDF Library
    2.6.2 Address Resolution Service
3. External Interface Requirements
3.1 User Interfaces
3.2 Hardware Interfaces
3.3 Software Interfaces
3.4 Communications Interfaces
4. System Features
4.1 Administer System
    4.1.1 Description
    4.1.2 Stimulus/Response Sequences
    4.1.3 Functional Requirements
4.2 Administer Practice Configuration
    4.2.1 Description
    4.2.2 Stimulus/Response Sequences
    4.2.3 Functional Requirements
4.3 Maintain User/Group Accounts
    4.3.1 Description
    4.3.2 Stimulus/Response Sequences
    4.3.3 Functional Requirements
4.4 Maintain Practitioners
    4.4.1 Description
    4.4.2 Stimulus/Response Sequences
    4.4.3 Functional Requirements
4.5 Assign Workbaskets and Work
    4.5.1 Description
    4.5.2 Stimulus/Response Sequences
    4.5.3 Functional Requirements
4.6 Maintain Patient Profile
    4.6.1 Description
    4.6.2 Stimulus/Response Sequences
    4.6.3 Functional Requirements
4.7 Patient Matching
    4.7.1 Description
    4.7.2 Stimulus/Response Sequences
    4.7.3 Functional Requirements
4.8 Load Raw Documents
    4.8.1 Description
    4.8.2 Stimulus/Response Sequences
    4.8.3 Functional Requirements
4.9 Tag Documents
    4.9.1 Description
    4.9.2 Stimulus/Response Sequences
    4.9.3 Functional Requirements
4.10 Share Documents
    4.10.1 Description
    4.10.2 Stimulus/Response Sequences
    4.10.3 Functional Requirements
4.11 Search For, Select, and Download Documents
    4.11.1 Description
    4.11.2 Stimulus/Response Sequences
    4.11.3 Functional Requirements
4.12 p-Mail
    4.12.1 Description
    4.12.2 Stimulus/Response Sequences
    4.12.3 Functional Requirements
4.13 Jot-a-Doc
    4.13.1 Description
    4.13.2 Stimulus/Response Sequences
    4.13.3 Functional Requirements
4.14 Auditing
    4.14.1 Description
    4.14.2 Stimulus/Response Sequences
    4.14.3 Functional Requirements
4.15 Reporting
    4.15.1 Description
    4.15.2 Stimulus/Response Sequences
    4.15.3 Functional Requirements
4.16 Customer Billing Support
    4.16.1 Description
    4.16.2 Stimulus/Response Sequences
    4.16.3 Functional Requirement
4.17 Support Page
    4.17.1 Description
    4.17.2 Stimulus/Response Sequences
    4.17.3 Functional Requirements
5. Other Nonfunctional Requirements
5.1 Performance Requirements
5.2 Safety Requirements
5.3 Security Requirements
    5.3.1 Logins
    5.3.2 Password Constraints
    5.3.3 Connections
    5.3.4 Sessions
    5.3.5 Downloading
    5.3.6 Encryption
    5.3.7 Patient Information
    5.3.8 Temporary Files
5.4 Software Quality Attributes
5.5 Business Rules
5.6 User Documentation
6. Other Requirements
Index A: Glossary
Index B: Major Entities
Practice
Branch
User
Group
Permission (System Table, not updateable)
Practitioner
Patient
Patient Circle
Share
Raw File
Document
p-Mail
Audit
Index C: To-Be-Determined List
Import HL 7 Data
Data Archive Introduction 1.1 Purpose This document contains the current Software Requirements Specification (SRS) for the COYOTE product. This document defines and describes the interfaces, functions, performance, security and quality assurance requirements for COYOTE.

1.2 Document Conventions

Major entities of the COYOTE system are capitalized, e.g. Patient.

Attributes of a system entity, e.g. STATUS, are shown in SMALL CAPS.

Values of an entity attribute, e.g. Inactive, are shown in Italics. Boolean attributes whose name implies a value of True, when used without a value, are used with the value implied. For example, the statement "A Document flagged as EXTERNAL will automatically be flagged as KEEP PRIVATE" means "A Document flagged as EXTERNAL=True will automatically be flagged as KEEP PRIVATE=True".

Stimulus/Response sections in Section 4 list sequences of stimuli (events, user actions, or other triggers) and system functions that define the behaviors for the feature. They are representative of use cases.

1.3 Intended Audience and Reading Suggestions

This document is intended for all COYOTE stakeholders, including, but not limited to, developers, project managers, users, testers, and documentation authors for COYOTE. This SRS will be used as a common point of reference for understanding the capabilities to be provided by COYOTE.

This document is intended for internal use by The Parrot Group (TPG) and its employees, consultants, and other approved representatives. This document and all information contained herein may not be distributed to any party without a signed non-disclosure agreement or equivalent.

1.4 Product Scope

COYOTE is an Electronic Medical Records (EMR) system for health-care practices. It is offered to customers in an Application Service Provider (ASP) model, i.e. the system is provided as a turnkey, hosted solution to which users subscribe. Access to COYOTE is provided via the Internet and a web browser. COYOTE provides three major functions.

1. Document Uploading
   Uploading of customer files to the COYOTE workbasket
   Tagging and storage of uploaded files in the COYOTE database as Adobe Acrobat (.PDF) files
2. Document Sharing
COYOTE customers may share documents with other COYOTE customers in two ways:
   Explicit sharing of Documents with another Practitioner or Practice
   Joining a Patient's Circle of Care, where all participating Practices share Documents about a specific Patient
3. Document Retrieval
   Local (intra-practice) and global (inter-practice) searching
   Structured searches on all Document attributes
   Free-text searching on Document contents
   Documents retrieved by searches may be downloaded to the User's workstation for viewing in the Acrobat Reader.

1.5 References
2. Overall Description
2.1 Product Perspective

COYOTE is a stand-alone, ASP-based EMR system targeted to medical practices. COYOTE allows customers to share patient medical information without mailing, faxing, or courier services. It is intended to revolutionize the way medical practices share information about patients they treat in common.

This SRS represents the first attempt to define the requirements of COYOTE: a new system with no predecessors.

2.2 Product Functions

Various classes of users will have the ability to perform the following functions:

2.2.1 System Administrative Functions
   Administer System
   Administer Practice Configuration
   Audit Activity For Customer Invoicing
2.2.2 Practice Administrative Functions
   Maintain User/Group Accounts
   Maintain Practitioners
   Audit User Activity For HIPAA Compliance And Security 2.2.3 Practice Management Functions
   Assign Workbaskets and Work
   Maintain Patient Profile
2.2.4 Document Management Functions
   Load Raw Documents
   Tag Documents
   Share Documents
   Jot-a-Doc
   Search For, Select, and Download Documents
   p-Mail
   Reporting
2.3 User Classes and Characteristics
   The Global Administrator has total control over the entire system.
   A System Administrator sets up new Practices and deactivates a Practice that is no longer a subscriber.
   A Practice Administrator has control over local settings, Users, Groups, and Permissions.
   A User has the ability to process Patient and Document records.
   A Practitioner is a special type of User who has the additional ability to produce Jot-a-Docs and receive p-Mails.
2.4 Operating Environment COYOTE is based on an ASP model. There will be a single instance of COYOTE hosted on a set of centralized servers connected to the Internet. Users will access COYOTE over the Internet with a web browser.

COYOTE servers must provide file system services, database management services, and web services.

No specific hardware or software platforms have been specified for COYOTE. However, any platforms chosen must be highly scaleable, with the ability to ultimately support thousands of practices and millions of documents. Scalability may be achieved by replacing existing servers with those of higher capacity, or by augmenting existing servers with additional servers via aggregation and load balancing.

While COYOTE does not require advanced capacity management technologies such as storage area networks and hierarchical storage management, it should not preclude their use as its storage requirements expand.

2.5 Design and Implementation Constraints

COYOTE will be implemented in easily acquired, widely used, industry standard tools and platforms. Proprietary technology will be specified only on an exception basis.

COYOTE will store and deliver Document data in Adobe Acrobat (.PDF) format.

COYOTE will employ a relational database to store structured data.

COYOTE will communicate with client workstations via HTTP and HTTPS.

COYOTE will support clients running Microsoft Internet Explorer Version 5.1 or higher.

A source code control system will be used to maintain all COYOTE source code.

Source code will be written and formatted uniformly according to a standard. All COYOTE source code modules will contain a standard header, identifying the author, date, and module, as well as a functional description. All source code modules will also contain the date, author and description of each modification performed subsequent to initial development.

Use of browser plug-ins, applets, and Active-X controls is strongly discouraged, as they will reduce the acceptability of COYOTE in the marketplace. The single exception to this guideline at this time is the use of the Adobe Acrobat viewer, which will be required to view downloaded documents, and thus, integral to COYOTE's function.

Because of security and privacy concerns, COYOTE will not interface with standard email systems, except to email p-Mail arrival notifications to Practitioners whose email addresses are entered in the Practitioner profile.

2.6 Assumptions and Dependencies 2.6.1 PDF Library

A server-based PDF function library with an API that will allow:

Creation, concatenation and splitting of PDF files

Ability to create PDF files with user-defined password protection

Ability to create PDF files with JBIG2 compression

Ability to create PDF files with a user-defined background or logo.

2.6.2 Address Resolution Service

A server-based service that will:

Return a USPS formatted address, given any user-entered address.

3. External Interface Requirements 3.1 User Interfaces

The complete specification of the COYOTE user interface will be defined during the design phase of the project. However, some portions of the UI specification currently exist and are documented here, to be carried forward to the design phase.

All COYOTE user interface components will be implemented in a web browser environment.

The COYOTE user interface will bear the COYOTE brand, so that users always know they are using COYOTE. The interface will be customized so that users can also see the name of the practice they are logged into.

Minimum screen resolution supported is 1024×768.

Practice or Branch Favorites Lists. A Practice-wide or Branch-wide list of commonly used items that typically appear in drop-down lists. Only Practice Administrators (PA's) may explicitly alter the contents of the lists.

Favorites lists as well as the MPL will provide a mechanism whereby the User may filter Inactive Practitioners. By default, these lists will present only Active Practitioners.

User Preferences

A User will be able, from any primary screen, to select one or more Branches for the purpose of filtering Patients and Documents in system listings. At logoff, the last filter selected will be saved as a User PREFERENCE.

Search criteria will default to the last search the User performed during his current session. At logoff, parameters of the last search performed will be saved as a User PREFERENCE.

Dropdown boxes will provide standard keystroke indexing capability.

Circle of Care Traffic Signal. In the Patient profile, a graphic resembling a traffic signal will indicate the Practice's local level of participation in the Patient's Circle:

Green indicates that the Practice participates in the Patient's Circle.

Yellow indicates that a Circle exists, but the Practice does not participate even though the Patient's local chart is not KEEP PRIVATE.

Red indicates that the Patient's local chart is KEEP PRIVATE.

Circle of Care List.

If a Practice participates in a Circle of Care, then in the Patient profile, a list of other Practices who participate in the Circle will be available. If Documents of a Practice that once participated but has since withdrawn from the Circle are still available to the Circle, that Practice will also be listed, along with its withdrawal date and a visual indicator such as a tombstone.

If a Practice once participated in a Circle of Care, but has since withdrawn, then in the Patient Profile there will be a visual indicator such as a tombstone along with the withdrawal date.

Jot-a-Docs may be stored on User-defined, electronic "letterhead" to allow Users to customize the look of electronically created Documents.

Users may define subfolders within their p-Mail inbox.

Users will have the option to log out of COYOTE from all primary screens.

There will be a link to the COYOTE support page on all primary screens.

3.2 Hardware Interfaces

None specified.

3.3 Software Interfaces

None specified.

3.4 Communications Interfaces

COYOTE will communicate with client web browsers via standard HTTPS protocol, utilizing 128-bit encryption. The COYOTE web service must install a signed digital certificate from a widely recognized certification authority such as Verisign.

4. System Features 4.1 Administer System 4.1.1 Description

COYOTE System Administration includes setting up Practices, editing an existing Practice, and deactivating an existing Practice. It also includes maintenance of system-wide settings as well as global tables.

User Classes: Global Administrator, System Administrator 4.1.2 Stimulus/Response Sequences New customer subscribes→Add Practice Existing customer changes billing information→Edit Practice Existing customer requires change to file size maximums→Edit Practice Customer requests dump of files Copy Files to Portable Media Existing customer cancels subscription→Deactivate Practice COYOTE system requires change to file size or idle timeout maximums→Change System Setting New Work Type needed→Add Work Type Users need to acknowledge reading new EULA→Reset EULA flags 4.1.3 Functional Requirements A System Administrator will set up a new customer by creating a Practice and creating a Practice Administrator User Account for the Practice.

A Practice's BILLING ADDRESS and BILLING INFO may be edited as needed.

A Practice's FILE UPLOAD MAX and DOCUMENT MAX may be changed as needed.

A Practice may request that all its files be copied to portable media. This will be a TPG service offering. When a dump of files is requested by a Practice, an accompanying flat file will list all Documents, along with identifying information. An additional flat file will list all Patients of the Practice, along with their demographic data.

A COYOTE customer that wishes to cancel its subscription to the COYOTE service may request backups of its files (see above). A System Administrator will change the Practice STATUS to Inactive, which will, in turn, set the STATUS of all the Practice's Practitioners to Inactive. In addition, participation of the Practice in any Patient Circles will be withdrawn.

Global system settings for maximum file upload size and maximum Document size may be set.

Global system settings for maximum idle timeout may be set.

New values for Work Type may be added.

A System Administrator may reset EULA ACKNOWLEDGEMENT to False for all Users so that when they log in, they will be required to acknowledge reading the EULA.

4.2 Administer Practice Configuration 4.2.1 Description

Administration of Practice Configuration includes maintenance of Practice options and Practice tables.

User Class: Practice Administrator 4.2.2 Stimulus/Response Sequences

New customer→Select options for Practice, Edit Practice tables

Practice desires change to configuration→Change Practice options, Edit Practice tables 4.2.3 Functional Requirements Practice options govern the behavior of the system from the time they are set. The Practice Administrator will set the options at system initialization and may change the settings at any time. The options are:

Security options (see Section 5.3)

Default HIPPA KEEP PRIVATE setting for new Patient records (system default is True)

Document of WORK TYPE HIPPA required before Patient HIPPA KEEP PRIVATE flag may be changed BRANCH is required on Document PRACTITIONER is required on Document PRACTITIONER is required on Document when the author is external to the Practice Practice KEEP PRIVATE flag Default Workbasket Threshold for deletion of Raw Files Default p-Mail receiver Elapsed time for changing Patient STATUS to Inactive At system initialization, values may be added to Practice level code tables. Values may be added to these tables at any time. Values may be deleted only if they are not in use (referenced by other entities in the system).

Branch

Case Type

Keywords

Workbaskets

Favorites List (Practice, Branch)

4.3 Maintain User/Group Accounts 4.3.1 Description

Maintenance of User and Group Accounts includes adding, editing, and assigning permissions to accounts.

User Class: Practice Administrator 4.3.2 Stimulus/Response Sequences

New customer→Add Groups, Assign Permissions to Groups, Add Users, Assign Users to Groups, Assign Permissions to Users New user→Add User, Assign User to Groups, Assign Permissions to User Shut down user→Disable User Restore user→Enable User Change group authorization→Change Group Permissions Change user authorization→Change User Permissions 4.3.3 Functional Requirements The Practice Administrator may define Practice level Groups. Five Groups will be system-defined and may not be changed:

Global Administrator

System Administrator

Practice Administrator

Practitioner

User

Users will be defined by the PA and may contain system access restrictions (see Section 5.3).

User Accounts may be deactivated, but not deleted.

The PA may shut down or restore a User at any time by disabling or enabling the User Account.

Permissions will be system-defined and may not be changed. Permission checking will be real-time.

A PA may assign Permissions to Users and to Practice-defined Groups. Permissions are:

Add Practice (reserved for System Administrator Group)

Edit Practice (reserved for System Administrator Group)

Add Patient Profile

Edit Patient Profile

Upload Raw File

Delete Raw File

Tag Document

Override Patient "Keep Private" Flag

Local Search

Global Search

Full-text Search

Download Document

Share Document

Send Local p-Mail

Receive Local p-Mail

Send Local and Non-local p-Mail from Tagging/Search Forms

Send and Receive Non-local p-Mail (reserved for Practitioner Group)

Jot-a-Doc (reserved for Practitioner Group)

View Audit Reports 4.4 Maintain Practitioners 4.4.1 Description

Maintenance of Practitioners includes adding and editing Practitioner information.

User Class Practice Administrator 4.4.2 Stimulus/Response Sequences

New Practitioner→Add Practitioner

Practitioner leaves Practice→Deactivate Practitioner, Reassign Patients to Another Practitioner Practitioner temporarily absent→Assign Another Practitioner to Receive Copies of p-Mails Practitioner requests Jot-a-Doc template→Upload Template, Assign Template to Practitioner 4.4.3 Functional Requirements All Practitioners in COYOTE will appear on the Master Practitioner List that displays both Practice and Practitioner name. An Inactive Practitioner will show on the Master Practitioner List as inactive with a visual indicator such as a tombstone.

A new Practitioner may be added to a Practice. A Practitioner/Practice association will be unique in the system.

A Practitioner at a Practice may be deactivated, but not deleted.

The PA may select all Patients for a particular Practitioner and assign them to another Practitioner, either individually, or in batch.

The PA may set up a Practitioner to receive copies of p-Mail for a vacationing or absent Practitioner.

Jot-a-Doc templates may be uploaded to COYOTE and associated with Practitioners.

4.5 Assign Workbaskets and Work

4.5.1 Description

Raw Files that have been uploaded but not yet tagged are associated with a Workbasket. Workbaskets may be assigned to Users, and Work may be assigned to a Workbasket.
User Class: Practice Administrator

4.5.2 Stimulus/Response Sequences

User requires work assignment→Assign Workbasket
Work needs to be delegated→Assign Work to Workbasket, Assign Workbasket to User
Raw Files need to be deleted→Delete Raw File

4.5.3 Functional Requirements

The WORKBASKET assigned to a User may be changed.
The WORKBASKET to which a Raw File is assigned may be changed.
The PA may delete Raw Files that Users have assigned to the "trash basket".
The PA may delete processed or unprocessed Raw Files explicitly. When Raw Files reach Practice-set aging thresholds, they will be deleted by the system.

4.6 Maintain Patient Profile

4.6.1 Description

Maintaining Patient demographic data includes adding and editing Patient information. Much of this data controls the implicit and explicit sharing of Patient Documents.
User Classes: Practice Administrator, Practitioner, and User

4.6.2 Stimulus/Response Sequences

New patient→Add Patient Profile for Practice
Patient makes HIPPA election→Edit HIPPA KEEP PRIVATE Attribute
Practice makes decision to keep all Patient records Private→Edit KEEP PRIVATE Attribute
Practice makes decision to share with Circle→Edit SHARE WITH CIRCLE Attribute
User wishes to see Circle participation→View Patient Profile
Patient changes demographic information→Edit Patient Profile
Patient elects Branch or Practitioner preference→Edit Patient Profile
Patient leaves Practice or dies→Change STATUS

4.6.3 Functional Requirements

User will create and edit Patient attributes for the Practice.
New Patient profiles will default to SHARE WITH CIRCLE=False and KEEP PRIVATE. The HIPPA KEEP PRIVATE attribute will default to the Practice's option.
A warning message will be presented when any change is made to the KEEP PRIVATE attribute.
If the Practice setting dictates it, the HIPPA KEEP PRIVATE flag may not be updated unless there is at least one Document with WORK TYPE of HIPPA for the Patient.
Any change to Patient Address (STREET, CITY, STATE ZIP) will insert the old address into a PRIOR ADDRESS attribute. Any change to LAST NAME will insert the old name into a PRIOR LAST NAME attribute. Any change to HOME TELEPHONE or MOBILE TELEPHONE will insert the old number into a PRIOR TELEPHONE attribute.
In order to standardize addresses, an address resolution service will be utilized.
Any change to an attribute that is used for Patient Matching will trigger the Patient Matching algorithm. If the result causes the Patient to leave a Patient Circle, the system will:
  Create a new Patient record and mark the old Patient STATUS as Inactive.
  Make copies of all the Patient's Documents and relate them to the new Patient record.
  Set DISREGARD on all the old Documents.
  Set DISREGARD REASON to Patient demographic changes on all old Documents.
  Create a Document for the old Patient with WORK TYPE of Correspondence that contains the message "Patient has left this Circle due to 'identifying' demographic changes".
  Link the Patient to a Patient Circle, if a match exists, or create a new Patient Circle.

The Patient profile may be edited to add or change Patient preferences regarding Branches and Practitioners.
A Practice may elect to share Documents for a particular Patient with all other COYOTE Practices who share the same Patient. This is accomplished by setting a SHARE WITH CIRCLE flag on the Patient.
When viewing the Patient profile, a User will be able to see the local level of participation in the Patient's Circle of Care as well as a list of other Practices who participate in the Circle (see Section 3.1).
A Practice may elect to disallow sharing for all Documents for a particular Patient. This is accomplished by setting a KEEP PRIVATE flag on the Patient.
If a Patient leaves the Practice, his profile may be marked as Inactive; if he dies, his profile may be marked as Deceased.
Access to the Patient profile will be available during tagging, sharing, and p-Mailing. Given the prerequisite Permission, a User may also edit the profile during these activities. A User may search for Patients by specifying Patient attributes.

4.7 Patient Matching

4.7.1 Description

Patient Matching is a system algorithm that is triggered by the change of Patient demographic data. It attempts, based on sets of parameters, to find any other Patients in the system that appear to be the same person.
User Classes: Practice Administrator, Practitioner, and User

4.7.2 Stimulus/Response Sequences

User saves a new Patient profile→Patient Matching
User commits changes to an existing Patient profile→Patient Matching

4.7.3 Functional Requirements

When changes are made to any data used in Patient Matching, this algorithm will be triggered. This process will determine whether the Patient matches an existing PATIENT ID.
If there is no match, then a new Patient Circle will be created with this Patient's demographic data.
In either case (Patient Circle is created or joined), the Patient profile will be updated with the PATIENT ID of the Patient Circle. Additionally, the Patient Circle will be updated with the PRACTICE and an indicator as to whether the Practice is participating or not in the Circle of Care for this PATIENT ID.
The Patient Matching algorithm will return a match if all data in any one of the following identification parameters matches:
  DOB and SSNR and GENDER
  DOB and SSNR and Address
  DOB and SSNR and Telephone
  DOB and SSNR and FIRST NAME
  DOB and SSNR and Last Name
In the above criteria, Address includes STREET, CITY, STATE, and ZIP CODE, as well as all PRIOR ADDRESSES. Telephone includes HOME TELEPHONE and MOBILE TELEPHONE as well as all PRIOR TELEPHONES. Last Name includes LAST NAME as well as all PRIOR LAST NAMES.

4.8 Load Raw Documents

4.8.1 Description

Files from a User's local computer may be uploaded into COYOTE.
User Classes Practice Administrator, Practitioner, and User

4.8.2 Stimulus/Response Sequences

Practice desires to turn a file into a COYOTE document→Upload File

File is not suitable for tagging→Trash File

4.8.3 Functional Requirements

User will select a file or group of files from the local hard drive for upload into COYOTE. As they are uploaded, they will be concatenated, converted to PDF format, and saved as a Raw File. This Raw File will be assigned the WORKBASKET of the uploading User but may be reassigned by the PA.

A Raw File may be sent to a "trash basket", which means that it may be deleted by the PA.

System-level and Practice-level settings will limit the size of files that may be selected for upload.

4.9 Tag Documents

4.9.1 Description

Tagging is the act of breaking off part of a Raw File, formatting it, assigning properties to it, and saving it as a Document.

User Classes: Practice Administrator, Practitioner, and User

4.9.2 Stimulus/Response Sequences

Practice requires patient records to be filed→Tag Document

Document is saved in error→Change Document to DISREGARD

Document is filed incorrectly→Retag Document

4.9.3 Functional Requirements

No text or copy may be altered in or added to a Raw File. During tagging, however, the pages of a Raw File may be rotated, sorted, and/or deleted.

Pages of a Raw File may be selected for saving as a Document.

Tagging a Document (the selected pages of a Raw File) associates it with a Patient, a date of service, and other attributes listed in Appendix B. When tagging is finished for the Document, it is saved and committed.

Documents will default to KEEP PRIVATE when a Practice is flagged as KEEP PRIVATE.

A Document will default to KEEP PRIVATE for a Patient whose profile indicates KEEP PRIVATE and a warning message will be given if this attribute is changed.

A Document tagged as EXTERNAL will automatically be tagged as KEEP PRIVATE.

A Document with WORK TYPE of either HIPPA or Admin (Administrative) will be tagged automatically as KEEP PRIVATE.

When a User tags a Document with WORK TYPE of HIPPA, the User will be given the opportunity to change the Patient's HIPPA KEEP PRIVATE flag.

When a User tags a Document, the User will be given the opportunity to update the SHARE WITH CIRCLE flag to True for the selected Patient.

When a User tags a Document, the User will be able to see all Practices that have shared a Document for this Patient. Once the tagged Document is saved, the User may select all, several, or none of the listed Practices with whom to share the current Document.

System-level and Practice-level settings will limit the size of Documents that may be saved.

A Document saved in error may have its DISREGARD flag set and a free-form DISREGARD REASON may be entered.

Retagging a Document places a copy of the document into the workbasket, changing the original Document's DISREGARD flag to True, and allows the User to add a DISREGARD REASON description to explain why it is to be disregarded.

Users will have the ability to p-Mail a newly tagged Document from the tagging form.

Once a page of a raw file is associated with a Patient, subsequent pages are also associated with that Patient until the tagging user specifies another Patient or the end of the Document. In this way, raw files containing multiple Patient Documents can be easily separated by moving sequentially through the raw file.

4.10 Share Documents

4.10.1 Description

Documents from one Practice may be shared with another COYOTE Practice.

User Classes Practice Administrator, Practitioner, and User

4.10.2 Stimulus/Response Sequences

Practice requests that Patient chart be shared with another Practice→Share Patient Chart Practice requests that a Document be shared with another Practice→Share Document

4.10.3 Functional Requirements

Sharing is between Practices. There are two types, based on whether the Patient is common to both Practices and those Practices have elected to have the Patient records shared.

Implicit

Participating Practices that share a Patient (see Patient Matching) whose SHARE WITH CIRCLE flag is True automatically have access to any Documents not marked KEEP PRIVATE for that Patient. This is the Patient Circle (Circle of Care).

A Practice, when participating in a Patient's Circle of Care, shares with the Circle not only its local Documents, but also all other Documents that are or have been shared with it.

Implicit shares are extended when one Practice sends a p-Mail with attached Document to another.

Explicit

Patient Documents may be shared with another Practice even if that Practice does not share the Patient. The target Practice can view the shared document only if it has a profile for the Patient. Otherwise, the share still exists, but the Document cannot be viewed. The only way a Practice may view Documents for Patients for whom they do not have profiles is via p-Mail.

When sharing is attempted for a Patient whose HIPPA KEEP PRIVATE flag is True, the system sends a warning, but does not issue a lockout. In other words, the Practice may override the Patient's stated HIPPA election.

When a Document is shared, permission to view that Document is extended to the target Practices. If the Document is subsequently marked as KEEP PRIVATE, or if the sharing Practice withdraws from a Patient Circle, the existing permissions to share the Document are not rescinded. Sharing a document, whether implicitly or explicitly, is irrevocable. Conceptually, it is analogous to sending a physical copy of a document to another practice.

4.11 Search For, Select, and Download Documents

4.11.1 Description

A User may search for, select, and download Documents for which he has permission.

User Classes Practice Administrator, Practitioner, and User

4.11.2 Stimulus/Response Sequences

User needs to locate and download Document(s)→Search and Select and Download Document(s)

4.11.3 Functional Requirements

User may search for Documents by specifying Document attributes. By default, DISREGARDed Documents will not be included in the search, but the User may choose to include them. Permissions will control whether a User may search locally (within the Practice), globally, or do full-text searches. The resulting list may be sorted using multiple sort criteria. Each item in the resulting list will afford opportunity for the User to see the chart of the Patient involved.

The User may select a Document or multiple Documents for downloading. An Audit record will be created for every Document downloaded.

A download directed to the User's local file system will contain a cover page listing the search criteria and sort order, User and date/timestamp. The Documents will be concatenated in the same order as the list sort order.

4.12 p-Mail
4.12.1 Description

P-Mail is an electronic communication system that is internal to COYOTE. A p-Mail may include a message and it may have a link to one or more Documents.

User Classes: System Administrator, Practice Administrator, Practitioner, and User

4.12.2 Stimulus/Response Sequences

Practice wishes to share Document(s) with another Practitioner→Compose p-Mail

Practice wishes to alert another Practitioner of available Documents→Compose p-Mail User wishes to send a message and/or Documents to another User→Compose p-Mail User wishes to view message and/or Documents p-Mailed to him→Open p-Mail User wishes to organize his p-Mail→File p-Mail User wishes to share Documents and/or message in a p-Mail→Forward p-Mail System Administrator wishes to reply to Support request→Compose p-Mail User wishes to initiate a Support request→Compose p-Mail

4.12.3 Functional Requirements

With permission, Users may exchange p-Mail locally.

Sending p-Mail containing Documents, i.e. from the tagging or search forms, may be done with permission.

Sending p-Mail containing no Documents (message only) to an outside Practice is restricted to Practitioners except in the case of a System Administrator replying to a request from the Support page.

Receiving non-local p-Mail is restricted to Practitioners.

When the intended recipient of a Document is not in the Patient's Circle of Care, p-Mail is a link to a Document (or set of Documents) that is being explicitly shared. When the intended recipient is in the Circle of Care, p-Mail acts as an alert ("May I bring your attention to . . . ") and can be viewed via the p-Mail interface or via the Search and Select interface. A p-Mail header will consist of the SENDER, SUBJECT, MESSAGE, and DATE/TIMESTAMP. The User sending the p-Mail will choose the SENDER (required), SUBJECT (optional), MESSAGE (optional), and Documents (optional). A p-Mail may have multiple SEND TOs (addressees), but the recipient will see only his own name/Practice. Selection of a recipient for p-Mail will be from either a list of local Users who have permission to receive p-Mail or the MPL. Selecting a Practitioner from the MPL to receive a p-Mail will add that Practitioner to the Practice's (or Branch's) Favorites list, if not already there.

Non-local P-Mail must be directed to a Practice, and optionally to a Practitioner. If the Documents contained refer to only one Patient, then the p-Mail will be directed to the Practitioner designated in the profile of the Patient at the receiving Practice, overriding, if necessary, the SEND TO Practitioner. If the Documents contained refer to multiple patients, or there is no Practitioner listed in the Patient's profile, the p-Mail will be directed to the SEND TO Practitioner. Failing the foregoing identification of a Practitioner for direction, the p-Mail will arrive in the p-Mail "Inbox" of the Practice's default p-Mail receiver.

When a p-Mail is directed to a Practice where no Practitioner can be identified (e.g. there is no default Practitioner or the Practice is Inactive), the User will be notified that "P-Mail is not available at this Practice."

P-Mails may be saved, forwarded, and deleted. They may be organized into user-defined "Folders".

When a p-Mail is directed to a Practitioner who has an E-Mail address in COYOTE, an E-Mail will alert that Practitioner that he should check his p-Mail. This E-Mail will contain a message reminding the Practitioner how to turn off this automatic E-Mail notification.

Opening a p-Mail will display the message, if any, and list any enclosed Documents along with their descriptions. It will use the same interface (perhaps in a different color) as the Search For, Select, and Download process.

If there is no Patient match for a Document at the receiving Practice, a message "No match in your practice, do not delete p-Mail" will be displayed. Additionally, such a Document may be submitted to a Practice-defined general workbasket for tagging.

When a p-Mail is sent outside of the originating Practice, an implied share is created between the sending and receiving Practices for the Documents cited in the p-Mail.

4.13 Jot-a-Doc
4.13.1 Description

Jot-a-Doc is a facility for entering a Document directly into COYOTE without uploading a file.

User Class Practitioner

4.13.2 Stimulus/Response Sequences

Practitioner wishes to send a letter to another Practitioner→Send Jot-a-Doc

4.13.3 Functional Requirements

The input text may be merged into a template that is the Practitioner's letterhead. The Jot-a-Doc has all the properties of a Document, that is, it is tagged with the same attributes. The Practitioner may p-Mail this Document to another Practice or Practitioner.

The PA will be responsible for creating and uploading templates for Practitioners. A default template will be "From the Desk of . . . " with the Practitioner's name.

4.14 Auditing
4.14.1 Description

Audit records will be stored for reasons of tracking privacy as well for billing purposes.

User Classes Practice Administrator, Practitioner, and User

4.14.2 Stimulus/Response Sequences

User logs in→Store User Audit Record

User logs off→Store User Audit Record

User sends a message-only p-Mail→Store User Audit Record

File is uploaded→Store Raw File Audit Record

Document is committed→Store Document Audit Record

Document is modified→Store Document Audit Record

Document is downloaded→Store Document Audit Record

Document is p-Mailed→Store Document Audit Record

Jot-a-Doc is created→Store Document Audit Record

4.14.3 Functional Requirements

An Audit record will contain User, Date/timestamp, and Activity. It will also record Document and Patient, if the activity concerns them, and file size and description, when appropriate.

Only Users within the Practice of the user that caused the audit to be recorded may view audit data. The ability to view audit data is further restricted by Permission.

4.15 Reporting
4.15.1 Description

Reports, available for viewing and printing, relate to HIPPA Compliance, Document Shares, and Audits.

User Classes: Practice Administrator, Practitioner, and User
4.15.2 Stimulus/Response Sequences
User wishes to see everyone who has viewed a Patient's records→HIPPA Compliance Report
User wishes to know who has access to a particular Document→Document Shares Report
User wishes to view Audit records→Audit Report
4.15.3 Functional Requirements
The HIPPA Compliance Report will list every COYOTE User who has downloaded Documents for a given Patient. The requesting User will select a Patient. The report header will display the Practice, identifying Patient attributes, and date that the report was generated. The report will list Document, User, and date.
The Document Shares Report may be generated by the Practice owning the Document in question. The requesting User will select a Document. The report header will show the Practice, Patient, identifying Document attributes, and the date the report was generated. The report will list all Practices with access to the Document.
The Audit Report will list Audit information within a User's Practice. The requesting User may filter the listing by selecting from the following parameters: USER, date range, TYPE, DOCUMENT, PATIENT, and ACTIVITY. The report header will list the parameters chosen and the date the report was generated. The report will list the selected Audit records
4.16 Customer Billing Support
4.16.1 Description
Billing for some COYOTE customers will be based on COYOTE system statistics and usage.
User Class: System Administrator
4.16.2 Stimulus/Response Sequences
Monthly billing cycle→Generate Billing Report
4.16.3 Functional Requirement
COYOTE will support the billing function by providing reports formatted for easy import into other software programs. Billing report parameters will include customer and date and will provide the following information:
   Number of logins
   Number and size of file uploads
   Number and type of tagged documents
   Number and size of downloads
   Number of p-Mails sent (counted as number of recipients)
     (distinguish between local and to external p-Mails)
   Number of Jot-a-Docs created
   Number of documents on file
   Document data storage (in bytes)
   Document data storage per patient (in bytes)
   Number of defined users
   Number of branches
   Number of practitioners
4.17 Support Page
4.17.1 Description
A support page containing contact information for COYOTE will be available.
User Classes: Practice Administrator, Practitioner, and User
4.17.2 Stimulus/Response Sequences
User needs to know how to contact COYOTE→View Support Page
User wishes to submit a question to COYOTE personnel→Request for Information Form
User wishes access to a Practice that does not appear on the master list→Request to Add a Practice Form
4.17.3 Functional Requirements
A support page will contain information for contacting COYOTE personnel. It will list relevant addresses, telephone numbers, and fax numbers.
The support page will also have links to two forms that will send electronic requests to COYOTE personnel. One will be the Request for Information Form. Another will be the Request to Add a Practice Form. Both forms will contain a message assuring User that the request is not part of any medical record.
Replies to these requests may use the p-Mail facility.
5. Other Nonfunctional Requirements
5.1 Performance Requirements
COYOTE must be scaleable. While its initial implementation may have modest capacity, the business plan for COYOTE envisions rapid and massive growth up to thousands of medical practices (customers), tens of millions of documents, and thousands of concurrent online users.
Without the design specifications, it is impossible to say with specificity at this time what this means in terms of computer memory, processor cycles, disk storage, and database management system capacity. However, it is certain that the potential demands of COYOTE require selection of platforms that have the ability to scale to massive capacities.
COYOTE must be highly available. Because it is the repository for medical records involved in patient care, it must be available 7×24 with very low downtime tolerances (99.99999% available). While many factors influencing availability are outside the scope of this document, developers need to be aware that COYOTE must be running continuously, and design accordingly. At some point in its evolution, COYOTE may be deployed at multiple sites in order to improve its availability and performance. This also needs to be considered at design time.
When performing data entry functions, the server will respond to requests within 5 seconds. Due to network latency and other factors outside of the control of the COYOTE system, response time users experience may vary. Searching, uploading, downloading and reporting will not be subject to this requirement.
5.2 Safety Requirements
None specified.
5.3 Security Requirements
5.3.1 Logins
All Users will log into COYOTE with an assigned user id and password. There will be no anonymous access provided.
Upon initial login, a User will be required to read and acknowledge the EULA, and change their password. The acknowledgement of the EULA will be recorded in the User's profile.
The PA will be able to set the number of consecutive invalid login attempts allowed before a Practice User account is disabled. Locked User accounts can be unlocked only by an administrator.
Administrators may lock individual User accounts or all Users of a Practice from logging into COYOTE. Locking an account will prohibit any further logins and will terminate any current sessions.
The PA may restrict logins by time of day on a practice-wide or individual User basis.
The PA may define a time interval for one-time access during which a given User may log in to COYOTE. Once the interval expires, the User may not use COYOTE again without PA intervention.
5.3.2 Password Constraints
The following password constraints will be controlled by the PA for each User:
   Password expiration (number of days)
   Password length and character composition (uppercase, lowercase, numerals, special characters).
   Ability for User to change his own password (yes/no)

Account disabled (does not allow logins)
Restrictions on previously used passwords
Passwords will be stored in the database in a one-way encrypted format. They will never be displayed on screen. Users' passwords will not be visible or readable under any circumstances. The remedy for a lost password is for an administrator to reset it. Administrators may reset Users' passwords at any time.

5.3.3 Connections

The PA may restrict connections by masked IP address for individual Users.

5.3.4 Sessions

When Users log into COYOTE, they will be assigned to a session that allows their login to be tracked, and temporary information about their work on the system to be stored on COYOTE. Idle time between user interactions with COYOTE will be tracked. Sessions that exceed a system-wide maximum idle timeout will be terminated and Users will be forced to log into COYOTE before they can use the system again. PA's will be able to define a practice-wide idle timeout that does not exceed the system-wide setting.

In order to identify a User with their session, COYOTE will store a cookie on the User's browser that contains the session key. Session keys will be randomly generated and will have no other semantic content.

5.3.5 Downloading

Users will have the option to password-protect any .PDF file they download.

5.3.6 Encryption

Except for user login passwords, data will be stored in the COYOTE system without encryption.

Downloaded files will be stored unencrypted on the User's workstation.

All data traveling between the COYOTE server and a COYOTE client will be protected with SSL 128 bit encryption.

5.3.7 Patient Information

Patient information is the property of a Practice. By definition, all Practice users have unrestricted read-only access to all of their Patient records and Documents. Permission to update Patient profiles is granted to Practice Users and Groups by the PA.

Users outside of a Practice may view Patient documents via sharing. Sharing is initiated by the owning Practice by:
  Sending a p-Mail
  Creating an explicit share between a local Document and another Practice having a profile for the same patient.
  Joining a Patient's Circle of Care (implicit sharing of all local, non-KEEP PRIVATE Patient Documents with all other Circle participants)

Patient Documents that are marked KEEP PRIVATE may not be shared without an override.

If a Patient profile is marked KEEP PRIVATE, then no shares may be created for any Patient Documents without an override.

When a Practice joins a Circle of Care it shares not only its local Documents, but also all global Documents to which it ever had viewing permission.

Patient profiles may never be viewed by Users outside of the Practice.

Patient Document content can never be changed under any circumstances.

A Practice may not initiate sharing of a Patient's Documents without the Patient's permission (except in the case of an override). In COYOTE, the uploading of a permission form, tagged as WORK TYPE HIPAA, and acknowledging the Patient's permission to share their records is required to enable sharing. Conversely, a Patient may revoke their permission to share by submitting an additional form.

5.3.8 Temporary Files

During a COYOTE session, the client web browser may retain pieces of COYOTE web pages in memory or on disk after those pages have been removed from the User's view. How this information is cached is dependent on the implementation of the particular type and version of web browser being employed. It is impossible for COYOTE to insure that the web browser's cache is emptied after the conclusion of a session, so users should be trained to take appropriate precautions to insure compliance with privacy and security policies.

Once a COYOTE Document has been downloaded to a User's browser as a file, COYOTE has no further control over that file, and it becomes the sole responsibility of the User to safeguard the file's contents according to applicable privacy and security policies.

5.4 Software Quality Attributes

None specified.

5.5 Business Rules

None specified.

5.6 User Documentation

See Section 4.17.

6. Other Requirements

INDEX A

Glossary

ASP Application Service Provider
Circle of A collection of Practices who have a Patient in common as determined by
Care matching demographic data
Client Any workstation connected to the COYOTE service over the Internet with a compatible web browser
DOB Date of Birth
Document A PDF file that has been tagged and committed
EIN Employer Identification Number, Tax ID
EMR Electronic Medical Records
EULA End User License Agreement
Jot-a-Doc A Document that has been entered into the system directly, rather than uploaded
MPL Master Practitioner List
MRN Medical Record Number—Patient/case number, internal to a Practice
NPI National Provider Identifier
p-Mail A messaging system that is internal to COYOTE, optionally containing a link to a Document or set of Documents
PA Practice Administrator
Patient All Patient Documents to which a Practice has access. This includes local
Chart and shared Documents
Patient Practice-level attributes of a Patient
Profile
PDF Portable Document Format
Raw File A PDF file that has been uploaded, but not tagged
Server Any server computer responsible for hosting any part of the COYOTE service
SSNR Social Security Number
SOAP Note Subjective Objective Assessment Plan—a method for taking medical notes
SRS Software Requirements Specification
Tag Define (assign properties to) a Document
TPG The Parrot Group
Work Unprocessed Raw Files
UPIN Universal Physician Identifier Number

INDEX B

Major Entities

The major entities of the COYOTE system and some of their attributes are listed here as an aid to understanding system requirements. The complete entity-relationship specification will be developed during the design phase of the project.

TABLE 1

Practice

| | |
|---|---|
| EIN | Unique identifier |
| NPI | National Provider Identifier. Unique. 10-digit |
| STATUS | Active, Inactive |
| NAME | |
| ADDRESS INFO | |
| PHONE NUMBERS | |
| BILLING ADDRESS | |
| BILLING INFO | |
| FILE UPLOAD MAX | Maximum size of a file that may be uploaded into COYOTE |
| DOCUMENT MAX | Maximum size of a file that may be stored as a Document |
| KEEP PRIVATE | Boolean |
| BRANCHES | Multiple |
| USERS | Multiple |
| PRACTITIONERS | Multiple |
| PATIENTS | Multiple |
| SETUP OPTIONS | Multiple |
| FAVORITES LIST | Multiple |

TABLE 2

Branch

| | |
|---|---|
| NAME | |
| PRACTICE | |
| ADDRESS INFO | For display in MPL |
| FAVORITES LIST | Multiple |

TABLE 3

User

| | |
|---|---|
| USER ID | Logon. Unique within Practice. |
| PASSWORDS | |
| NAME | |
| PRACTICE | |
| TYPE | Clerical, Practitioner |
| STATUS | Active, Inactive |
| DISABLED | Boolean |
| LOGIN TIME OF DAY | |
| EULA ACKNOWLEDGEMENT | Boolean |
| WORKBASKET | |
| PERMISSIONS | Multiple |
| PREFERENCES | Multiple (Default Branch, Last Search parameters) |

TABLE 4

Group

| | |
|---|---|
| NAME | Global Administrator, System Administrator, Practice Administrator, Practitioner, and User are reserved. At least one user from a Practice must belong to the Practice Administrator Group. |
| PRACTICE | Only for Practice-defined Groups. |
| DESCRIPTION | |
| PERMISSIONS | Multiple |

TABLE 5

Permission (System Table, not updateable)

| | |
|---|---|
| NAME | Global to system |
| TYPE | |
| VALUE | |

TABLE 6

Practitioner

| | |
|---|---|
| UPIN | Unique identifier |
| NPI | National Provider Identifier. Unique. 10-digit |
| NAME | |
| STATUS | Active, Inactive |
| PRACTICE | |
| E-MAIL | |
| REDIRECT TO | Another Practitioner to whom p-Mail should be copied |
| BRANCHES | Multiple |
| TEMPLATE | Jot-a-Doc template |

TABLE 7

Patient

| | |
|---|---|
| PRACTICE | |
| MRN | |
| FIRST NAME | Used in Patient Matching |
| LAST NAME | Used in Patient Matching |
| STREET | Used in Patient Matching |
| CITY | Used in Patient Matching |
| STATE | Used in Patient Matching |
| ZIP CODE | Used in Patient Matching |
| HOME TELEPHONE | Used in Patient Matching |
| MOBILE TELEPHONE | Used in Patient Matching |
| FAX | |
| EMERGENCY CONTACT | Free-form text |
| BLOOD TYPE | |
| DOB | Used in Patient Matching |
| SSNR | Used in Patient Matching |
| GENDER | Used in Patient Matching |
| STATUS | Active, Inactive, Deceased |
| HIPPA KEEP PRIVATE | Boolean. Give warning message for HIPPA document when changing setting. |
| KEEP PRIVATE | Boolean |
| SHARE WITH CIRCLE | Boolean |
| BRANCHES | Multiple |
| PRACTITIONERS | Multiple |
| VIEWER LIST | Multiple. Audit records. |
| CIRCLE PATIENT ID | Set by Patient Matching algorithm. |
| PRIOR LAST NAMES | Multiple |
| PRIOR ADDRESSES | Multiple |
| PRIOR TELEPHONES | Multiple |

TABLE 8

Patient Circle

| | |
|---|---|
| PATIENT ID | Unique in entire system |
| FIRST NAME | Used in Patient Matching |
| LAST NAME | Used in Patient Matching |
| STREET | Used in Patient Matching |
| CITY | Used in Patient Matching |
| STATE | Used in Patient Matching |
| ZIP CODE | Used in Patient Matching |
| HOME TELEPHONE | Used in Patient Matching |
| MOBILE TELEPHONE | Used in Patient Matching |
| DOB | Used in Patient Matching |

TABLE 8-continued

Patient Circle

| | |
|---|---|
| SSNR | Used in Patient Matching |
| GENDER | Used in Patient Matching |
| CIRCLE PRACTICES | Multiple. Includes participation indicator. |

TABLE 9

Share

| | |
|---|---|
| PRACTICE | |
| PATIENT | |
| DOCUMENT | |
| SHARE WITH | Practice |

TABLE 10

Raw File

| | |
|---|---|
| IDENTIFIER | |
| DATE UPLOADED | |
| PRACTICE | |
| PROCESSED | Boolean |
| TRASH | Boolean |
| WORKBASKET | |

TABLE 11

Document

| | |
|---|---|
| PRACTICE | |
| BRANCH | Required (Practice Option) |
| PATIENT | |
| PRACTITIONER | Practitioner. Required (Practice Option). |
| EXTERNAL AUTHOR | Boolean |
| DATE | Date of Service |
| WORK TYPE | One per document. Required. Valued from System table. Values: Correspondence, Progress Notes, Studies, Problem List, HIPPA, and Billing. This field may be modified after tagging. |
| CASE TYPE | One per document. Required. Default to General. Valued from Practice table. |
| KEYWORDS | Multiple. Valued from Practice-defined table. |
| DESCRIPTION | Free-form text |
| DISREGARD | Boolean |
| DISREGARD REASON | Free-form text. Set to Patient has left this Circle due to demographic changes when Patient demographic changes result in a change to his Patient Identity. |
| KEEP PRIVATE | Boolean. Defaults to True if Practice-level KEEP PRIVATE is True or Patient's KEEP PRIVATE is True. Set to True when EXTERNAL AUTHOR is True. Set to True when WORK TYPE is either HIPPA or Billing. |
| TAGGING USER | |
| CREATE DATE/TIMESTAMP | System generated |
| LAST MODIFIED DATE/TIMESTAMP | System generated |
| LAST VIEWED DATE/TIMESTAMP | System generated |
| EXPLICIT SHARES | Multiple |
| FILE SIZE | |

TABLE 12 p-Mail

| | |
|---|---|
| SEND To | Multiple |
| SENDER | Required. Default to User. For non-local recipient, User may choose a Practitioner from the Practice. |
| SUBJECT | Optional |
| MESSAGE | Optional |
| DATE/TIMESTAMP | System generated |
| DOCUMENTS | Optional. Multiple |

TABLE 13

Audit

| | |
|---|---|
| PRACTICE | Practice |
| USER | |
| DATE/TIMESTAMP | |
| TYPE | User, Raw File, Document |
| DOCUMENT | |
| PATIENT | |
| FILE SIZE | |
| ACTIVITY | Login, Loge, Uploaded, Created, Modified, Downloaded, p-Mailed, Jot-a-Doc |
| DESCRIPTION | |

Index C: To-Be-Determined List

Items in this section are currently under consideration, but are not part of the formal requirements. They are listed here for a variety of reasons, including incomplete definitions or the need for further research or discussion. These items will not appear in subsequent design and construction phases without a change order.

Import HL 7 Data

COYOTE will be capable of accepting files in HL7 format from external systems. Received HL7 files will be translated into .PDF format based on a template composed for each specific vendor/message type combination. Incoming files generated from HL7 messages will be placed into the default workbasket of the designated practice for tagging. The received HL7 data file will be preserved and associated with the document that was generated from it. Specifications of data transmission are unique to each vendor. There are currently no requirements for support of specific vendors.

Requirements for importing data in HL7 need to be completed.

Data Archive

Because the central theme of COYOTE is Document sharing, there are constraints on removing data from the system. No Patient records or Documents will ever be deleted from COYOTE. Documents will, however, be archived when there is no activity in the Patient Circle for a period of time. Timing formulae for when Patient charts may be archived need to be researched and developed.

In the entire Patient's Circle, any Document that is opened will reset the archival timer. When there has been no activity for the time specified by formula, the complete set of Documents will be archived. ARCHIVED flags will be set on Patient profiles at all Practices belonging to the Circle.

By making a request to the System Administrator, a Practice may ask for a Patient's chart to be brought back online.

End of Appendix A

That which is claimed is:

1. A method of exchanging documents among multiple medical practices relating to common patients, comprising the steps of:
   (a) receiving, by a centralized server, from a first medical practice:
      (i) first documents relating to a first patient of the first medical practice,
      (ii) at least two types of first personal identification information of the first patient,
      (iii) first consent preferences of the first patient indicating whether the first patient consents to the first medical practice sharing the first documents with other medical practices, and
      (iv) first sharing preferences of the first medical practice, wherein the first sharing preferences indicate whether the first medical practice is willing to share at least some of the first documents with other medical practices and wherein the first sharing preferences are independent from the first consent preferences;
   (b) receiving, by the centralized server, from a second medical practice:
      (i) second documents relating to a second patient of the second medical practice, and
      (ii) at least two types of second personal identification information of the second patient;
   (c) determining, by the centralized server, whether the first patient is the same person as the second patient if two or more types of the first personal identification information match two or more types of the second personal identification information;
   (d) relating the second documents and at least some of the first documents in a database if the first patient is the same person as the second patient, the relating based, at least in part, on the first consent preferences and the first sharing preferences;
   (e) receiving, by the centralized server, from the second medical practice, a request to retrieve documents associated with the second patient; and
   (f) granting access to the second medical practice to view the second documents and the at least some of the first documents, wherein the second documents and the at least some of the first documents are presented together to the second medical practice if the first sharing preferences indicate that the first medical practice is willing to share the first medical records with other medical practices and the first consent preferences indicate that the first patient does not prohibit sharing the first medical records with other medical practices.

2. The method of claim 1, wherein at least one of the first and second medical practices is a pharmacy, insurer, hospital, laboratory or provider of nursing services.

3. The method of claim 1, further comprising:
   (g) receiving, by the centralized server, from a third medical practice:
      (i) third documents relating to a third patient of a third medical practice, and
      (ii) third consent preferences of the third patient indicating whether the third patient consents to the third medical practice sharing the third documents with other medical practices, and
   (h) preventing, by the centralized server, any other medical practice from viewing the third documents if the third consent preferences prohibit sharing the third documents.

4. The method of claim 1, further comprising the steps of:
   (g) receiving, by the centralized server, from the first medical practice an update to the first consent preferences revoking the first patient's consent to sharing the first medical documents with other medical practices;
   (h) preventing, by the centralized server, access by any other medical practice to the first patient's documents received from the first medical practice after the revocation;
   (i) preventing, by the centralized server, access to the first documents by other medical practices that have not yet accessed the first documents; and
   (j) continuing to grant access, by the centralized server, to the second medical practice if the restricted information received before the revocation was accessed by the second medical practice prior to the revocation.

5. The method of claim 1, further comprising the steps of:
   (g) receiving information from the first medical practice marking one or more of the first documents as private; and
   (h) preventing, by the centralized server, access by any other medical practice to the first documents marked private.

6. The method of claim 5, further comprising the steps of:
   (i) receiving information marking a private document as non-private; and
   (j) granting, by the centralized server, access to each other medical practice entitled to access such document but for its former status as private.

7. The method of claim 1, further comprising receiving, from the second medical practice, second consent preferences and second sharing preferences, the method further comprising:
   (g) determining, by the centralized server, whether the first medical practice and the second medical practice are members of a circle of sharing with respect to the first patient, wherein the circle of sharing for the first patient is dynamically generated based on the first and second personal identification information and the first and second sharing preferences; and
   (h) granting access, by the centralized server, to the first medical practice to the first documents and at least some of the second documents wherein the first documents and the at least some of the second documents are presented together to the first medical practice.

8. The method of claim 7, further comprising the step of:
   (i) identifying, by the centralized server, one or more additional medical practices that are part of the circle of sharing for the first patient; and (j) granting access, by the centralized server, to all members of the circle of sharing with respect to the first patient to the at least some of the first documents and the at least some of the second documents.

9. The method of claim 8, further comprising the step of:
(k) granting access, by the centralized server, to all members of the circle of sharing with respect to the first patient to all unrestricted received documents with respect to the first patient received at any time.

10. The method of claim 8, further comprising the step of:
(k) sending, by the centralized server, at least one of the first documents to each medical practice in the circle of sharing.

11. The method of claim 8, further comprising the step of:
(k) publishing a listing identifying each of the medical practices in the circle of sharing.

12. The method of claim 11, further comprising the step of:
(l) publishing a listing identifying practitioners employed by the medical practices in the circle of sharing.

13. The method of claim 11, further comprising the step of:
(l) publishing a listing identifying each of the medical practices formerly participating in the circle of sharing.

14. The method of claim 1, wherein the first documents and the second documents are stored in a secure medium.

15. The method of claim 14, wherein the secure medium comprises a file transport method employing encryption and authentication.

16. The method of claim 1, wherein the first patient is determined to be the same person as the second patient if one or more predetermined mandatory types of personal identification match and at least one of a plurality of secondary types of personal identification match.

17. The method of claim 1, further comprising the steps of:
(g) prompting a user to perform a local or global search;
(h) prompting the user to enter at least one search term;
(i) performing a search for documents based on data entered by the user in response to steps (g) and (h); and
(j) providing the results of step (i) to the user.

18. The method of claim 1, wherein historical information relating to the patient is used in part in determining whether the first patient is the same person as the second patient.

19. The method of claim 18, wherein the historical information includes at least one of the patient's former name, patient's gender, former address, secondary address, former telephone number, secondary telephone number, secondary e-mail address, and former email address.

20. A system for exchanging documents among multiple medical practices relating to common patients, the system comprising:
(a) a receiving interface configured for receiving:
  (i) first documents relating to a first patient of the first medical practice,
  (ii) at least two types of first personal identification information of the first patient,
  (iii) first consent preferences of the first patient indicating whether the first patient consents to the first medical practice sharing the first documents with other medical practices,
  (iv) first sharing preferences of the first medical practice, wherein the first sharing preferences indicate whether the first medical practice is willing to share at least some of the first documents with other medical practices and wherein the first sharing preferences are independent from the first consent preferences,
  (v) second documents relating to a second patient of the second medical practice,
  (vi) at least two types of second personal identification information of the second patient, and
  (vii) receiving from the second medical practice, a request to retrieve documents associated with the second patient;
(b) a secure medium configured for storing:
  (i) the first and second documents, and
  (ii) the first and second personal identification information;
(c) a processor configured for:
  (i) determining whether the first patient is the same person as the second patient if two or more types of the first personal identification information match two or more types of the second personal identification information, and
  (ii) relating the second documents and at least some of the first documents in a database if the first patient is the same person as the second patient, the relating based, at least in part, on the first consent preferences and the first sharing preferences;
(d) an output interface configured for granting access to the second medical practice to view the second documents and the at least some of the first documents, wherein the second documents and the at least some of the first documents are presented together to the second medical practice if the first sharing preferences indicate that the first medical practice is willing to share the first medical records with other medical practices and the first consent preferences indicate that the first patient does not prohibit sharing the first medical records with other medical practices.

21. The system of claim 20, wherein the processor is further configured for:
(iii) determining that one or more predetermined mandatory types of personal identification information match and at least one of a plurality of secondary types of personal identification information match.

* * * * *